(12) United States Patent
Wang

(10) Patent No.: US 8,905,545 B2
(45) Date of Patent: Dec. 9, 2014

(54) TEAR FILM AND CONTACT LENS EVALUATION BY OPTICAL REFLECTOMETRY TECHNIQUE

(75) Inventor: Michael Renxun Wang, Miami, FL (US)

(73) Assignee: New Span Opto-Technology Inc.

( * ) Notice: Subject to any disclaimer, the term of this patent is extended or adjusted under 35 U.S.C. 154(b) by 264 days.

(21) Appl. No.: 13/342,814

(22) Filed: Jan. 3, 2012

(65) Prior Publication Data

US 2013/0169933 A1 Jul. 4, 2013

(51) Int. Cl.
*A61B 3/14* (2006.01)
*A61B 3/10* (2006.01)
*A61B 3/12* (2006.01)

(52) U.S. Cl.
CPC ............. *A61B 3/14* (2013.01); *A61B 3/1225* (2013.01)
USPC .......................................... 351/221; 351/206

(58) Field of Classification Search
USPC ........................................ 351/205, 206, 221
See application file for complete search history.

(56) References Cited

U.S. PATENT DOCUMENTS

| 2006/0109423 A1* | 5/2006 | Wang ............................ 351/206 |
| 2011/0069279 A1* | 3/2011 | Hacker et al. ................. 351/221 |
| 2011/0299034 A1* | 12/2011 | Walsh et al. .................. 351/206 |
| 2014/0104574 A1* | 4/2014 | Grenon et al. ................ 351/206 |

* cited by examiner

*Primary Examiner* — Mahidere Sahle

(57) ABSTRACT

A method and system for evaluation tear film thickness and thinning dynamics in an eye with or without wearing a contact lens using a specially configured optical reflectometer. The method and system may address the beam aiming flexibility on the tear film surface by incorporation of a galvanometer scanner with the fiber coupled optical reflectometer. The tear film thickness, tear film thinning dynamics, and tear film breakup thickness can be determined. The system can also be combined with spectral domain OCT or swept source OCT for ophthalmology applications. The advantage is fast and high precision tear film evaluation that can also be extended to water film on contact lens evaluation for the determination of contact lens hydrophilic properties.

20 Claims, 7 Drawing Sheets

TEAR FILM AND CONTACT LENS EVALUATION BY OPTICAL REFLECTOMETRY TECHNIQUE

STATEMENT REGARDING FEDERALLY SPONSORED RESEARCH OR DEVELOPMENT

The project research is sponsored by the National Institute of Health.
Assignee: New Span Opto-Technology Inc.

CROSS-REFERENCE TO RELATED APPLICATION n/a

FIELD OF THE INVENTION

The present invention relates to non-contact optical measurement of tear film thickness in an eye with or without wearing of contact lens using optical reflectometry technique.

BACKGROUND OF THE INVENTION

Dry eye syndrome (DES) is an ocular disease caused by the lack of tear flow or excessive tear loss due to evaporation. It is often caused by aging, environmental factors (such as windy weather), fatigue of eyes, as well as nutrition imbalance. Ocular discomfort and irritation are common symptoms of the DES. Wearing contact lens of poor hydrophilic or wettability properties may also result in DES and eye discomfort. Clinical diagnosis of DES and quantifying its degree of severity is of great significance. However, currently there is lack of suitable user friendly precision technique to evaluate the tear film thickness, tear thinning dynamics, and tear breakup thickness.

Several techniques are currently available for direct tear film measurement in a live eye including the fluorescence technique by instilling saline-fluorescence to the tear, noninvasive optical interferometric method using wavelength dependent fringes, and optical coherence tomography (OCT). The fluorescence technique is invasive that may disturb the tear film. The existing OCT technique suffers from poor thickness evaluation accuracy and thus is not promising for tear film evaluation. The wavelength dependent fringe based noninvasive optical interferometric method offers good measurement accuracy but suffers currently from its bulk optics based critical optical alignment and handling.

Optical reflectometry is a maturely developed measurement technique for multilayer optical films. It has been widely used in industry for quantifying multilayer optical film thicknesses for quality inspection and assurance. The multilayer films that can be measured include dielectric, semiconductor, conductor, polymer, and photoresist. The basic requirement for using optical reflectometry technique for multilayer film evaluation is that the film to film boundary is optical quality, there is reasonable refractive index difference between adjacent film layers so that the reflection from the film boundary is visible by the measurement reflectometer, and the film layers are reasonably transparent.

Optical reflectometers have been commercially developed by a number of institutions including Filmetrics Inc., StellarNet Inc., Ocean Optics, and New Span Opto-Technology Inc. However, none of present optical reflectometers have been configured and used for tear film evaluation in an eye as well as water film hydrophilic property evaluation on a contact lens. This invention shows a solution to tear film evaluation in an eye with or without wearing contact lens using the optical reflectometry technique. It is also a solution to water film hydrophilic property evaluation on a contact lens. The fiber coupled optical reflectometer with galvanometer scanner should make the tear film evaluation including tear thickness, tear thinning dynamics, and tear breakup thickness operational friendly.

SUMMARY OF THE INVENTION

The present invention advantageously provides a method and system for easier measurement of tear film in an eye with or without wearing contact lens using a specially configured optical reflectometer. The method and system may address the beam aiming flexibility on the tear film surface by incorporating a galvanometer scanner with the fiber coupled optical reflectometer. The beam-aiming algorithm allows quick position of the measurement beam on the eye and acquires wavelength dependent tear film reflectance data in real time. The tear film thickness, tear film thinning rate, and tear breakup thickness can be determined with subsequent reflectometry evaluation of the wavelength dependent reflectance data using known refractive indices and absorption indices of each tear film, cornea, and contact lens layers. The advantage is fast and high precision tear film measurement using specially configured optical reflectometry technique. It is also a convenient method for evaluation of water film hydrophilic property on a contact lens.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
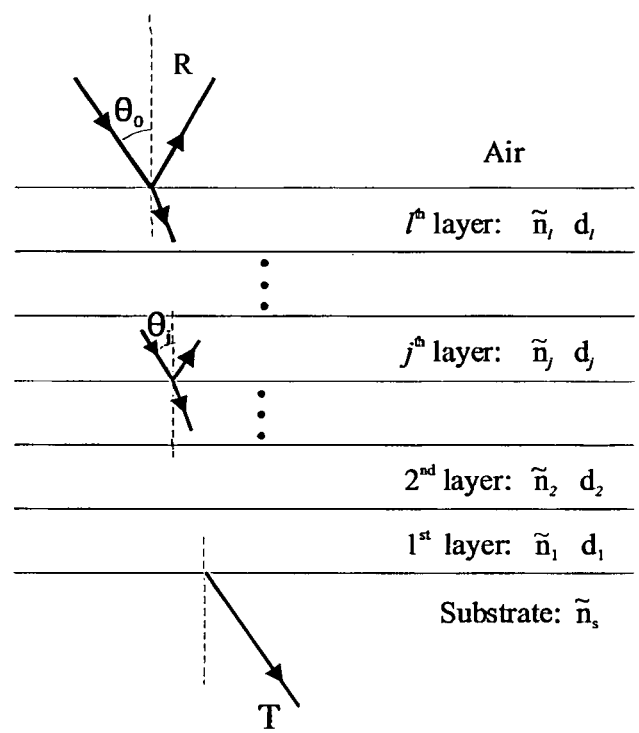
FIG. 1 shows a schematic representation of multilayer films surface reflection where the films are formed on the substrate for concept illustration.

Referring now to FIG. 1, the operation principle of fiber coupled optical reflectometer for multi-layer thin optical film evaluation can be briefly described as follows. An input light from a broadband light source, transmitted through a delivery fiber and collimated by an achromatic collimation lens, is illuminating in the surface normal direction on the multilayer films coated on a substrate. Because of the different complex refractive indices ñ (real refractive indices and imaginary absorption indices) of these film layers, there are reflections and transmissions from those film interfaces (including air/film and film/substrate interfaces). The subscript indicates the film layer or substrate. The multiple parallel film interface reflections and transmissions result in a net interferometric reflectance R and transmittance T which are wavelength dependent. The net reflected light is collected by the original collimation lens now focusing lens to a receiving optical fiber and then delivered to an optical spectrometer. With the use of a broadband light source such as a Tungsten Halogen light source, a spectral dependent reflectance $R(\lambda)$ is obtained from the optical spectrometer and sent to a computer. Processing this data through curve fitting using nonlinear least-squares numerical method (a predictor-corrector method) that is based on the principle of multilayer reflection in white light reflectometry determines the film thickness. For a single layer film, the system using the predictor-corrector method first estimates a film thickness d to initiate the reflectance calculation. The calculated and measured reflectance data are compared to determine the error. The computation process then continues to adjust the estimated thickness d for reducing error in each subsequent computation step until a minimum error is achieved when the calculated reflectance curve is best fit with the measured reflectance curve. For multilayer films, similar predictor-corrector curve fitting calculation with more thickness variables is performed. The numbers of film layers that can be determined are limited by the refractive index difference between adjacent film layers and the film quality. A standard reference sample such as a silicon wafer can be used to calibrate the light source spectral dependent emission and systematic error to ensure correct spectral dependent reflectance $R(\lambda)$ is acquired.

The optical reflectometer from New Span Opto-Technology Inc. has demonstrated a measurement error of less than 1 nm on a standard 200 nm thick $SiO_2$ film on Si substrate purchased from the US National Institute of Standard and Technology showing high measurement accuracy of the optical reflectometer. For a thicker film, the measurement accuracy should be governed by ±0.5% of the film thickness instead of the 1 nm according to the reflectometer specification. Thus, for a 1 μm thick film, the measurement accuracy should be ±5 nm or 10 nm. The measurement accuracy is excellent for tear film thickness evaluation.

Figure 2:
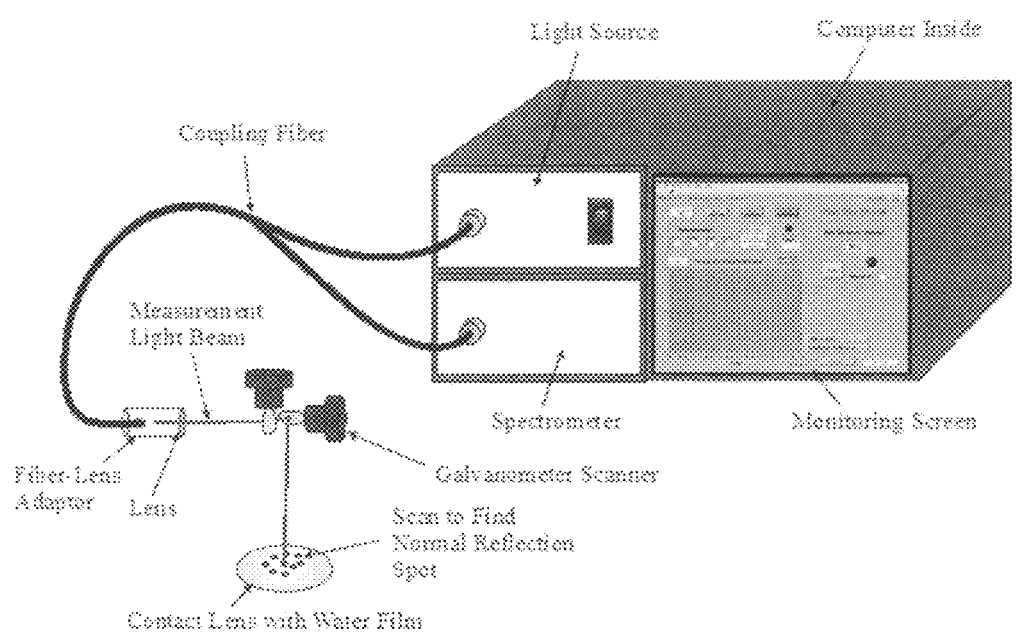
FIG. 2 shows a schematic representation of an optical reflectometer system with a galvanometer scanner having the functionality of quick measurement beam pointing to a curved contact lens surface for water film thickness evaluation.

Referring now to FIG. 2, a schematic representation of an optical reflectometer for evaluation of water film on a contact lens is shown. This serves as a phantom study of tear film evaluation in an eye. The system may include a broad band white light source, such as a Tungsten Halogen light source or a Xe arc lamp light source, an optical spectrometer, a coupling optical fiber, optical lenses, a computer, and a two-axis galvanometer scanner. A reflectometry software dynamically aims the measurement light beam through the galvanometer scanner to the water film on contact lens and acquires spectral dependent reflectance data from the water film as a function of time and perform subsequent determination of film thickness, film thinning rate, and film breakup thickness.

Figure 3:
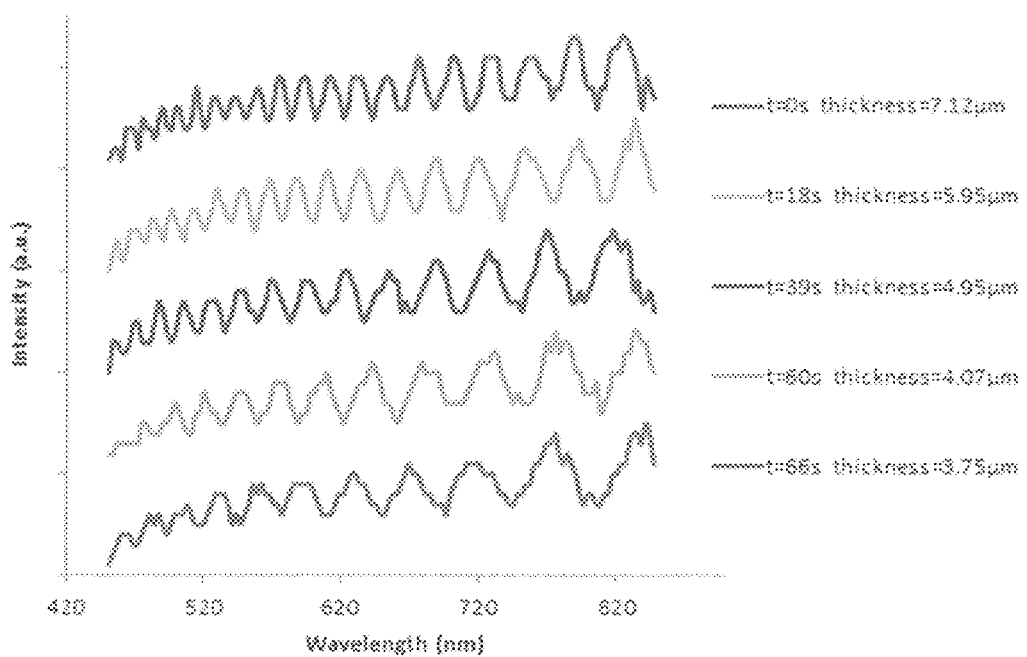
FIG. 3 shows spectral dependent reflectance curves acquired from a water film on a contact lens demonstrating water film thinning as a function of time.

Referring now to FIG. 3, the spectral dependent reflectance data from the water film on a contact lens are shown as measurement examples. The reflectance data are offset in vertical direction for illustration clarity. The water film on contact lens is a single layer film with curved contact lens surface. The measurement beam pointing through the two-axis galvanometer scanner should ensure enough film reflected light is received by the optical fiber for delivery to the optical spectrometer. During the measurement process, we observed that the reflectance curve (with maxima and minima) was moving consistently and slowly toward shorter wavelengths while its periods were increasing, indicating the water film was thinning with time. Since the water film is thinning with time, fast optical reflectometry measurement is required. The predictor-corrector curve fitting water film thickness determination is a complex computation process that may take time from sub second to a few seconds. Thus, we custom configured the optical reflectometer software to allow periodic saving of the measured spectral dependent reflectance data to external files and then perform the curve fitting thickness determination to reveal the water film thickness change process as a function of time. For different reflectance curve, its corresponding water film thickness is shown at right.

Figure 4:
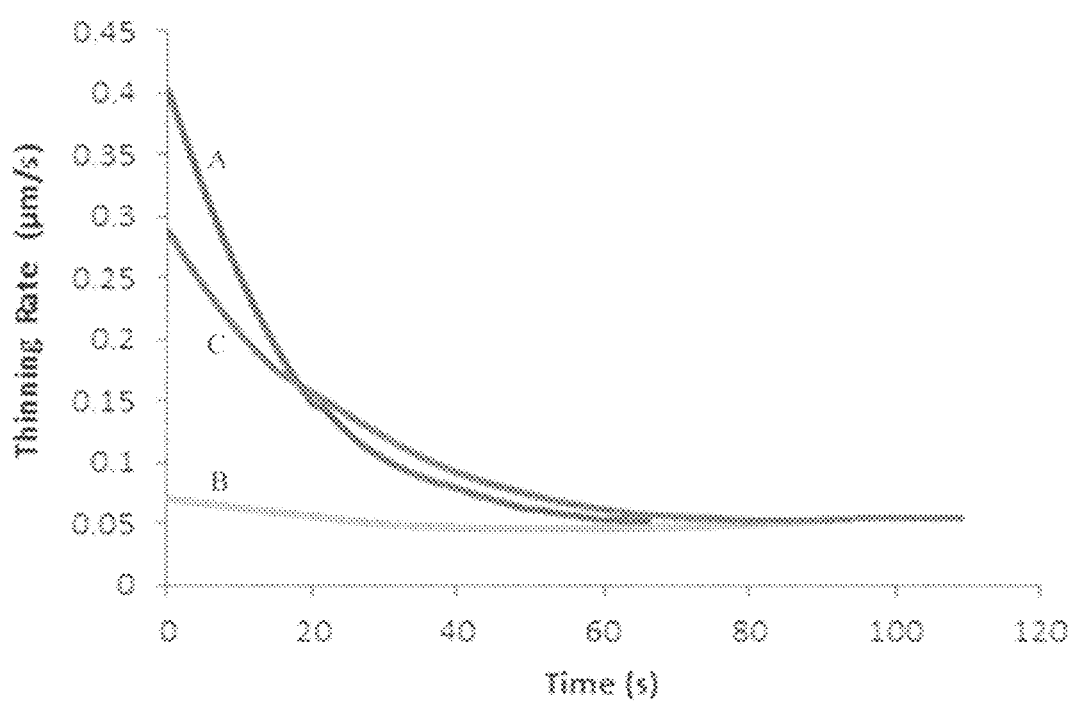
FIG. 4 shows different water film thinning rates obtained for different contact lenses A, B, and C by the measurement technique.

Referring now to FIG. 4, different water film thinning rate have been obtained for different contact lenses by the measurement technique. From each water film thinning curve, the initial water film thinning is found to be faster and it is slowing down with time that may be attributing to the water flow. When the water film is thick, its initial thinning process may attribute more to the gravity and contact lens shape related parameters and less related to the surface hydrophilic properties. We thus observed significant differences on initial water film thinning rate for different contact lenses. As the water film is thinning, the thinning rate is approaching to a steady state rate that may closely relate to the hydrophilic properties of the contact lens and water evaporation. The better the hydrophilic property and the smooth surface condition, the better the contact lens holding the water and the slower the water flow and water film thinning due to water evaporation. Therefore, the slower thinning rate in this stage may indicate the better contact lens hydrophilic property and smooth surface condition. Further water film thinning rate should ideally be the same due to similar water vaporization process till water film breakup. Clearly, the optical reflectometry technique may be useful for quantifying water film thinning dynamics for contact lens hydrophilic property evaluation.

Figure 5:
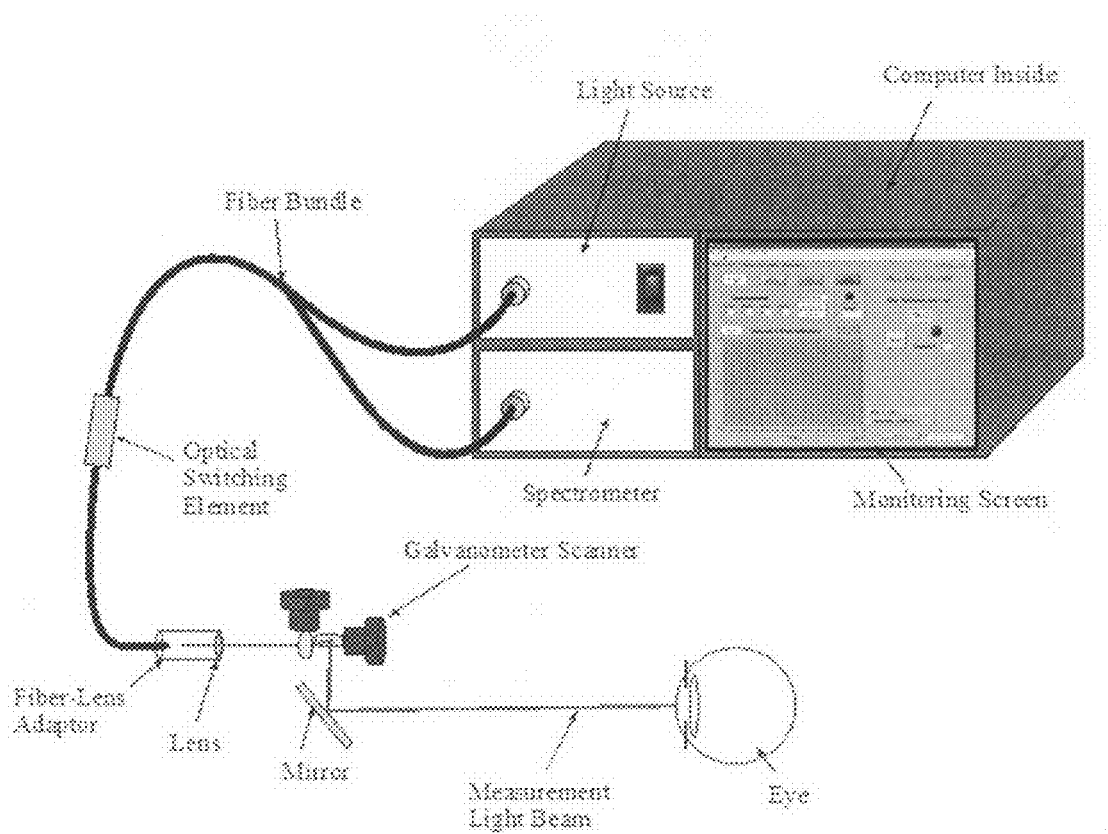
FIG. 5 shows a schematic representation of the optical reflectometer that is configured with a two-axis galvanometer scanner for tear film evaluation in an eye with or without wearing a contact lens.

Referring now to FIG. 5, the optical reflectometer is configured with a two-axis galvanometer scanner for tear film evaluation in an eye with or without wearing a contact lens. The use of galvanometer scanner may allow faster aiming of the measurement light beam to the eye for acquiring suitable wavelength dependent reflectance data from the tear film. The real time reflectance data can be saved to files for later tear film thickness, tear film thinning dynamics, and tear film breakup thickness evaluation. When wearing a contact lens, the tear films that can be measured may include pre-contact lens and post-contact lens tear films. We note that due to eye blinking that may happen before the tear film breakup, it is possible that the tear film breakup thickness may not be observable in a live eye. However, the measurement technique offers such measurement capability.

The use of broad spectral band white light has been found effective for water film on contact lens evaluation. For live eye tear film measurement, to minimize visible white light disturbance to an eye and subsequent eye movement affecting the measurement beam pointing, broad spectral band light source in the near infrared may be used. The corresponding optical spectrometer should be operating in the near infrared for effective acquisition of the near infrared wavelength dependent reflectance data for evaluation of tear film thickness and tear film thinning dynamics.

When using the broad spectral band white light for tear film evaluation, the white light disturbance to the live eye may also be avoided or minimized by using fast light flashing controlled by an optical shutter or an optical switching element, as shown in FIG. 5. In this way, the optical spectrometer for reflectance data acquisition should be synchronized through trigger control. Since the reflectance data acquisition can be a few milliseconds or faster, the corresponding fast measurement light beam on/off would have minimal effect to the live eye.

Figure 6:
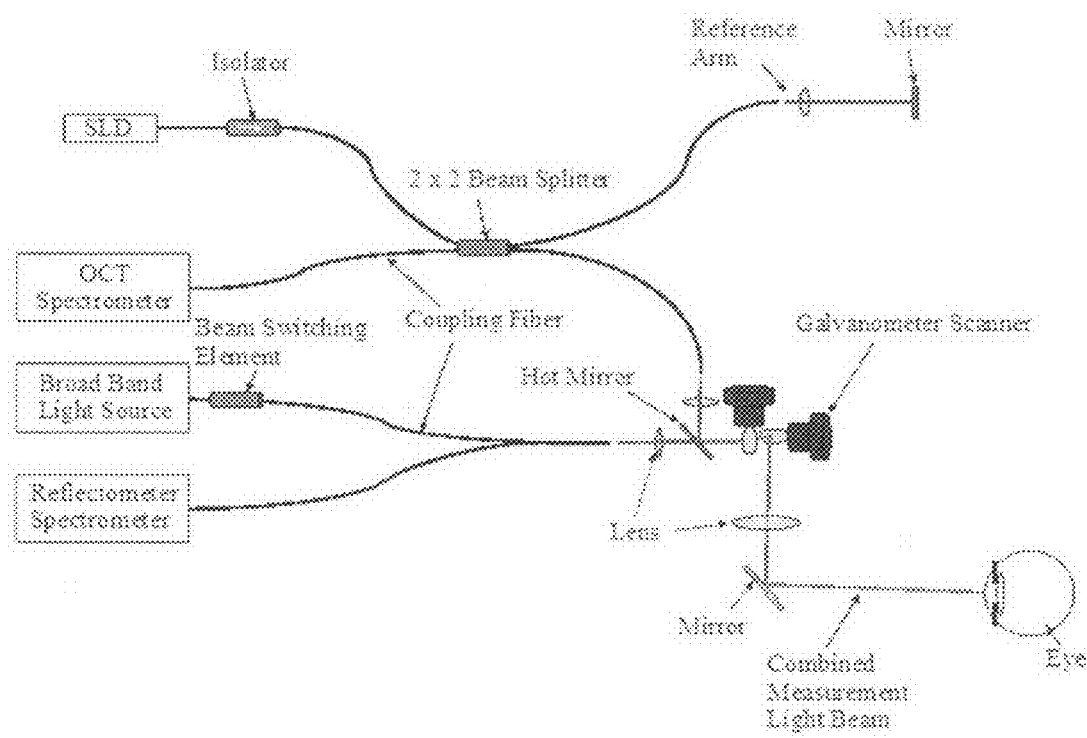
FIG. 6 shows a schematic representation of combining a spectral domain OCT with the tear film measuring optical reflectometer.

Optical coherence tomography is a non-contact and non-invasive imaging method that has been widely used for in vivo eye imaging. The combination of OCT and tear film evaluation optical reflectometer in a single measurement system may benefit ophthalmology applications. Referring now to FIG. 6, the schematic representation of combining a spectral domain OCT and the tear film measuring optical reflectometer is shown. The system may include a low-coherence light source, such as a superluminescent diode (SLD), a broad band light source, a beam splitter, a coupling fiber, a reference arm having one or more reference mirrors, a sample arm, one or more switching mirrors, one or more beam-switching elements, one or more imaging lenses, a diffraction grating, a spectrometer for OCT, a second spectrometer for tear film evaluation, and a digital signal processing unit. The tear film evaluation broad band light source and the spectrometer are turned on only when the shared galvanometer scanner is at the right position during OCT scanning for measurement beam pointing to the eye for tear film reflectance data acquisition and tear film thickness determination.

Figure 7:
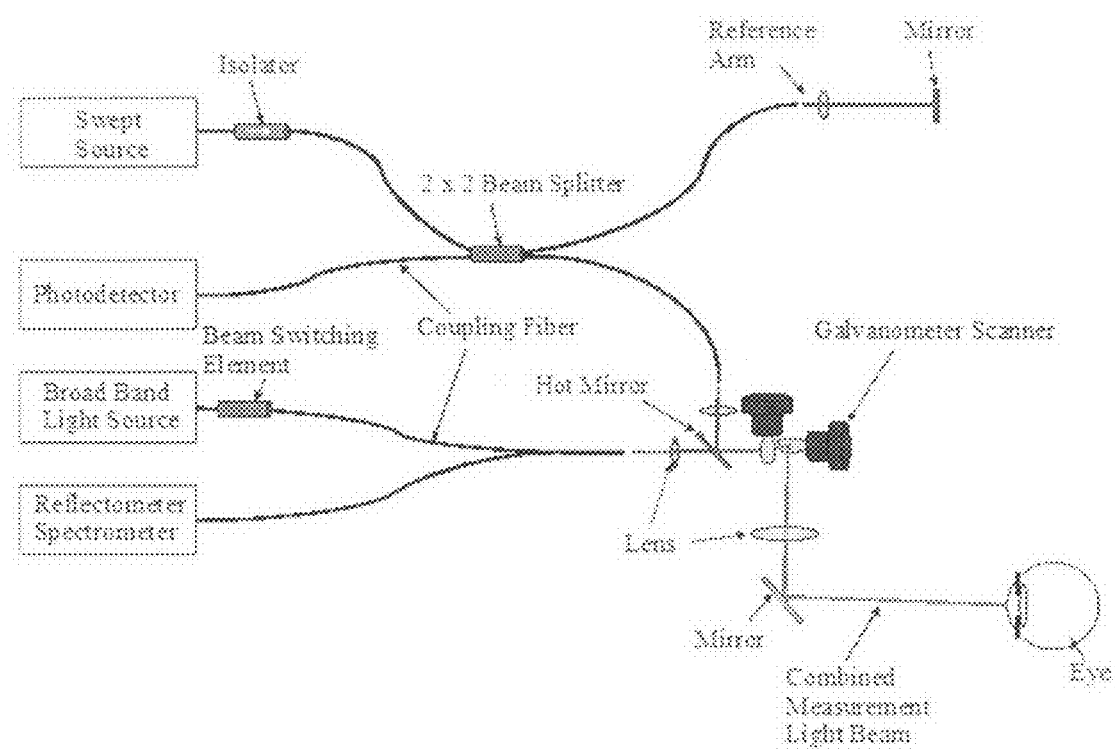
FIG. 7 shows a schematic representation of combining a swept source OCT with the tear film measuring optical reflectometer.

Referring now to FIG. 7, the schematic representation of combining a swept source OCT and the tear film measuring optical reflectometer is shown. The system may include a swept light source, a broad band light source, a beam splitter, a coupling fiber, a reference arm having one or more reference mirrors, a sample arm, one or more switching mirrors, one or more beam-switching elements, one or more imaging lenses, a photodetector, a spectrometer for tear film evaluation, and a digital signal processing unit. The tear film evaluation broad band light source and the spectrometer are turned on only when the shared galvanometer scanner is at the right position during OCT scanning for measurement beam pointing to the eye for tear film reflectance data acquisition and tear film thickness determination.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An optical apparatus comprising:
   an optical reflectometer configured to obtain an optical measurement of at least one film on a substrate wherein the at least one film varies its characters dynamically;
   wherein the at least one film is a tear film or an artificial tear film of at least one tear layer;
   a controller configured to control one or more beam scanning optics to acquire interferometric spectral reflectance signals; and
   a processor configured to analyze the reflectance signals to generate outputs of the characters of the at least one film.

2. The optical apparatus of claim 1, interferometric spectral reflectance signals are from the air, the at least one film, or substrate boundaries.

3. The optical apparatus of claim 1, wherein the substrate is cornea or a contact lens of at least one eye.

4. The optical apparatus of claim 1, wherein the substrate is a contact lens not in an eye.

5. The optical apparatus of claim 1, wherein the characters of the at least one film is the film layer thicknesses, film thinning rates, or film thickness statistics.

6. The optical apparatus of claim 1, the one or more beam scanning optics includes one or more synchronized galvanometer scan mirrors, or one or more synchronized micro-electro-mechanical-systems mirror scanners.

7. The optical apparatus of claim 1, the optical reflectometer uses a broad band light source.

8. An optical apparatus comprising:
   an optical reflectometer configured to combine with an optical coherence tomography apparatus configured for tomographic imaging and/or for optical measurement of at least one film on a substrate, wherein at least one film varies its characters dynamically;
   wherein the at least one film is a tear film or an artificial tear film of at least one tear layer;
   a controller configured to control one or more beam scanning optics to acquire interferometric spectral reflectance signals and acquire optical coherence tomography interferometric signals;
   a processor configured to analyze the reflectance signals to generate outputs of the characters of the at least one film; and
   a processor configured to analyze the optical coherence tomography interferometric signals to generate tomography images.

9. The apparatus of claim 8, wherein the substrate is cornea or a contact lens of at least one eye.

10. The apparatus of claim 8, wherein the substrate is a contact lens not in an eye.

11. The apparatus of claim 8, wherein the characters of at least one film is the film layer thicknesses, film thinning rates, or film thickness statistics.

12. The apparatus of claim 8, wherein the optical coherence tomography apparatus is a spectral domain optical coherence tomography system or a swept source optical coherence tomography system.

13. The apparatus of claim 8, the one or more beam scanning optics includes one or more synchronized galvanometer scan mirrors, or one or more synchronized micro-electro-mechanical-systems mirror scanners.

14. The apparatus of claim 8, the optical reflectometer light source and the optical coherence tomography light source are combined by a beam splitter optics or fiber optics.

15. The apparatus of claim 8, wherein the tomography image is the tomography image of the anterior segment of at least one eye.

16. A method, comprising:
   obtaining an optical measurement of at least one film on a substrate using an optical reflectometer, wherein the at least one film varies its characters dynamically;
   wherein the at least one film is tear film or artificial tear film of at least one tear layer;
   controlling one or more beam scanning optics to acquire interferometric spectral reflectance signals from the air, the at least one film, or substrate boundaries;
   and analyzing the reflectance signals to generate outputs of characters of the at least one film.

17. The method claim 16, wherein the substrate is cornea or a contact lens of at least one eye.

18. The method claim 16, wherein the substrate is a contact lens not in an eye.

19. The method claim 16, wherein the characters of at least one film is the film layer thicknesses, films thinning rates, or film thickness statistics.

20. The method claim 16, the one or more beam scanning optics includes one or more synchronized galvanometer scan mirrors, or one or more synchronized micro-electro-mechanical-systems mirror scanners.

* * * * *